United States Patent [19]

De Polo

[11] 4,387,089
[45] Jun. 7, 1983

[54] 4-(1,1-DIMETHYLETHYL)-4'-METHOXYDIBENZOYLMETHANE

[75] Inventor: Karl-Fred De Polo, Onex, Switzerland

[73] Assignee: Givaudan Corporation, Clifton, N.J.

[21] Appl. No.: 264,774

[22] Filed: May 18, 1981

Related U.S. Application Data

[63] Continuation of Ser. No. 92,777, Nov. 8, 1979, abandoned.

[30] Foreign Application Priority Data

Nov. 13, 1978 [CH]  Switzerland ..................... 11639/78
Aug. 23, 1979 [CH]  Switzerland ..................... 7686/79

[51] Int. Cl.$^3$ .................... C07C 49/245; A61K 7/42
[52] U.S. Cl. ..................................... 424/59; 568/331
[58] Field of Search ........................... 568/331; 424/59

[56] References Cited

U.S. PATENT DOCUMENTS 2,740,761  4/1956  Gleim ................................. 424/59
3,123,647  3/1964  Duennenberger et al. ........... 424/59
3,882,142  5/1975  Wolworth et al. ................. 568/331

FOREIGN PATENT DOCUMENTS 1473483  5/1977  United Kingdom ................. 424/59
1553094  9/1979  United Kingdom ................. 424/59

Primary Examiner—James H. Reamer
Attorney, Agent, or Firm—Robert F. Tavares

[57] ABSTRACT

The novel 4-(1,1-Dimethylethyl)-4'-methoxydibenzoylmethane is useful as a sunscreen agent. It exhibits outstanding UV-A absorbing qualities in that it brings about a considerable retardation in the ageing of the skin with excellent skin tolerance and stability (light, heat and moisture).

4-(1,1-Dimethylethyl)-4'-methoxydibenzoylmethane furthermore improves the protective action of UV B-filters, i.e. of substances which absorb the erythema-producing UV B-radiation in the range of about 290 to 320 mm.

17 Claims, No Drawings

4-(1,1-DIMETHYLETHYL)-4'-METHOXYDIBENZOYLMETHANE

This is a continuation of application Ser. No. 92,777 filed Nov. 8, 1979 now abandoned.

The present invention relates to light-screen agents.

It is known that sunlight accelerates the ageing of the skin, this undesirable effect being produced primarily by the UV A-radiation having wavelengths in the range of about 320 to 400 nm which directly tans the skin.

It has now been found in accordance with the present invention that 4-(1,1-dimethylethyl)-4'-methoxydibenzoylmethane, namely the compound of the formula

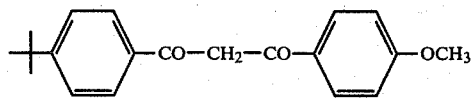

is an outstanding UV A-filter in that it brings about a considerable retardation in the ageing of the skin with excellent skin tolerance and stability (light, heat and moisture).

It has also been found in accordance with the present invention that the compound of formula I surprisingly improves the protective action of UV B-filters, i.e. of substances which absorb the erythema-producing UV B-radiation in the range of about 290 to 320 nm, although the absorption maximum of the compound of formula I does not lie in this range, but in the range of about 330 to 360 nm.

The present invention is based on the foregoing findings and is accordingly concerned in one aspect with light-screen agents containing the compound of formula I hereinbefore, preferably in combination with a UV B-filter. In another aspect, the invention is concerned with the use of the compound of formula I, preferably in combination with UV B-filters, in light-screen agents.

When the light-screen agents contain the compound of formula I in combination with a UV B-filter they completely absorb the UV-radiation in the range of 280 to 380 nm (described as a so-called "A+B total block") and protect the skin from premature ageing and in many cases from light dermatoses.

The manufacture of the light-screen agents provided by the present invention, especially of skin-protecting preparations for everyday cosmetics, is carried out by incorporating the compound of formula I, preferably in combination with a UV B-filter, in a cosmetic base which is customary for light-screen agents.

As UV B-filters in the scope of the present invention, i.e. as substances with absorption maxima between about 290 and 320 nm, there can be named customary UV B-filters such as, for example, the following organic compounds belonging to various classes of substances.

(1) p-Aminobenzoic acid derivatives such as, for example, ethyl p-aminobenzoate and other esters such as propyl, butyl and isobutyl p-aminobenzoate, ethyl p-dimethylaminobenzoate, glyceryl p-aminobenzoate and amyl p-dimethylaminobenzoate.

(2) Cinnamic acid derivatives such as, for example, 2-ethoxyethyl p-methoxycinnamic acid ester, 2-ethylhexyl p-methoxycinnamic acid ester, p-methoxycinnamic acid ester mixtures and cinnamic acid ester mixtures.

(3) Dibenzalazine.

(4) Heterocyclic nitrogen-containing compounds such as 2-phenylbenzimidazole derivatives (e.g. 2-phenylbenzimidazole-5-sulphonic acid).

(5) Salicylic acid derivatives such as, for example, salicylic acid menthyl ester, salicylic acid homomenthyl ester and salicylic acid phenyl ester.

(6) Benzophenone derivatives such as, for example, 4-phenylbenzophenone, 4-phenylbenzophenone-2-carboxylic acid isooctyl ester and 2-hydroxy-4-methoxybenzophenone-5-sulphonic acid. (7) Coumarin derivatives such as, for example, 7-hydroxycoumarin, β-umbelliferoneacetic acid, 6,7-dihydroxycoumarin.

(8) Gallic acid derivatives such as, for example, digalloyl-trioleate.

(9) Arylidenecycloalkanones such as, for example, benzylidenecamphor, p-tert.butylbenzylidenecamphor (preferred) and methylbenzylidenecamphor.

(10) Anthranilic acid derivatives such as, for example, anthranilic acid menthyl ester.

(11) Hydroxyphenylbenztriazole.

The compounds specified under (2) are preferred, particularly 2-ethylhexyl p-methoxycinnamic acid ester.

The cosmetic bases which are conventional for light-screen agents in the scope of the present invention can be any customary preparation which complies with the cosmetic requirements; for example, creams, lotions, emulsions, salves, gels, solutions, sprays, sticks, milks and the like, see also G. A. Nowak, Die Kosmetischen Präparate, 1st Edition 1969, 2nd Edition 1975 (Augsburg). The light-screen action is naturally also dependent on the base used. Furthermore, in the case of the same base the intensity of the light-screen action depends on the concentration of active substance. Suitable concentrations of the compound of formula I in the present light-screen agents lie, for example, between 1 wt. % and 6 wt. %, preferably between 2 wt. % and 5 wt. %. The ratio of the compound of formula I to the UV B-filter is not critical. On economical grounds it amounts, for example, to 1–2 parts of the UV B-filter to 1 part of the compound of formula I.

On the basis of its lipophility the compound of formula I can be incorporated well into oil-containing and fat-containing cosmetic preparations, an advantage which is not possessed by, for example, the compounds disclosed in DT-OS 25 40 798 such as dianisoylmethane (A). The compound of formula I is also superior to the light-screen agents disclosed in DT-OS 25 44 180, for example 4-isopropyl-[or 4-(1,1-dimethyl)]dibenzoylmethane (B,C). B and C do have good fat-solubility, but they absorb the UV A-radiation less ($\epsilon = 26344$ nm or 27396 at 347 nm, compared with 33866 at 355 nm for the compound of formula I. The compound of formula I has optimum properties with respect to adequate fat-solubility and absorption of the UV A-radiation.

The compound of formula I is novel and also forms part of the present invention. It can be manufactured according to the known methods of the Claisen condensation of an aromatic ester with a substituted acetophenone (see, for example, R. Hauser et al. in Organic Reactions Vol. VIII, page 59, John Wiley and Sons Inc., New York 1954), namely by reacting a compound of the formula

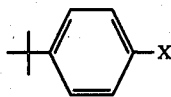

with a compound of the formula

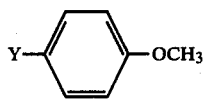

wherein in formulae II and III X represents a methoxycarbonyl group and Y represents an acetyl group or X represents an acetyl group and Y represents a methoxycarbonyl group.

The reaction of a compound of formula II with a compound of formula III is accordingly conveniently carried out in the presence of a strong base such as, for example, an alkali metal hydride (e.g. sodium hydride), an alkali metal amide (e.g. sodium amide) or an alkali metal alcoholate (e.g. sodium methylate or sodium ethylate).

The reaction is conveniently carried out in the presence of an inert solvent such as, for example, an ether (e.g. tetrahydrofuran) or a hydrocarbon (e.g. toluene). The reaction is conveniently carried out at a temperature of about 20°-70° C., especially about 50° C.

The isolation of the compound of formula I is preferably carried out by adding ice and an acid (e.g. a mineral acid or an alkanecarboxylic acid such as acetic acid) to the metal salt of the compound of formula I which separates as a solid precipitate, the thus-liberated compound of formula I then being obtained by concentrating the organic phase.

If necessary, the compound of formula I can be purified further by recrystallisation from a lower alcohol (e.g. methanol or ethanol).

The following Example illustrates the light-screen agents provided by the present invention:

EXAMPLE 1

| (a) Sun-screen cream, semi-fat (o/w) | Parts by weight |
|---|---|
| A: Stearic acid, triply pressed | 10.0 |
| Cetyl alcohol extra | 1.0 |
| Glycerine monomyristate | 5.0 |
| Isopropyl myristate (DELTYL EXTRA) | 7.0 |
| Oleyl alcohol, stabilised (SATOL) | 4.0 |
| 2-Ethylhexyl p-methoxycinnamic acid ester (PARSOL MCX) | 3.0 |
| 4-(1,1-Dimethylethyl)-4'-methoxydibenzoylmethane | 2.0 |
| B: Diethanolamine cetyl phosphate (AMPHISOL) | 3.0 |
| C: Distilled water | 58.8 |
| Propyleneglycol | 6.0 |
| Complex former (ethylenediaminetetraacetic acid, disodium salt) | 0.2 |
| D: Perfume 0.5% | q.s. |
| Preserving agent | q.s. |

The combined components of A are heated to 85° C. on a water-bath and B is added at this temperature. The mixture C is heated to 75° C. and added to the mixture of A and B. After cooling to 25°–30° C., any water losses are made up for and D is added.

| (b) Sun-screen cream for athletes (w/o) | Parts by weight |
|---|---|
| A: Non-ionic emulsifier (Arlacel 481) | 9.0 |
| Microcrystalline wax (Texwax MP 121) | 0.2 |
| DELTYL EXTRA | 1.0 |
| PARSOL MCX | 3.0 |
| 4-(1,1-Dimethylethyl)-4'-methoxydibenzoylmethane | 2.0 |
| B: Paraffin oil (d = 0.865–0.880) | 24.0 |
| Aluminium stearate (Alugel 30 DS 2) | 0.2 |
| C: Distilled water | 54.9 |
| Propyleneglycol | 5.0 |
| Magnesium sulphate dried | 0.5 |
| Complex former (ethylenediaminetetraacetic acid, disodium salt) | 0.2 |
| D: Perfume 0.5–1% | q.s. |
| Preserving agent | q.s. |

The mixture A is heated to 80° C. on a water-bath. The Alugel is dispersed in the paraffin oil at room temperature and this mixture is stirred until large particles disappear completely. Then, B is added to A and stirred until a homogeneous solution is obtained. C is heated to 75°–80° C. C is worked into the mixture of A and B with vigorous stirring. After cooling to 25°–30° C., the water losses are made up for and D is added. The resulting mixture is then homogenised.

| (c) Sun-screen milk (o/w) | Parts by weight |
|---|---|
| A: Stearic acid triply pressed | 3.0 |
| Vaseline oil (d = 0.849–0.866) | 6.0 |
| Diethyleneglycol monostearate | 0.5 |
| PARSOL MCX | 3.0 |
| 4-(1,1-Dimethylethyl)-4'-methoxydibenzoylmethane | 2.0 |
| B: AMPHISOL | 3.0 |
| C: Distilled water | 78.8 |
| Propyleneglycol | 3.0 |
| Pantothenyl alcohol (Panthenol) | 0.5 |
| Complex former (ethylenediaminetetraacetic acid, disodium salt) | 0.2 |
| D: Perfume 0.5% | q.s. |
| Preserving agent | q.s. |

The mixture A is heated to 80°–85° C. on a water-bath and B is then dissolved therein at this temperature. The mixture C is pre-heated to 75° C. and added to the mixture of A and B. After cooling to 25°–30° C., the water losses are made up for and D is added. The mixture is further stirred until a temperature of 25°–30° C. is reached.

| (d) Sun-screen milk (o/w) | Parts by weight |
|---|---|
| A: Cetyl alcohol | 1.0 |
| DELTYL EXTRA | 5.0 |
| Glycerine monomyristate | 4.0 |
| Arachis oil hydrogenated pharmacop. | 2.0 |
| PARSOL MCX | 1.0 |
| 4-(1,1-Dimethylethyl)-4'-methoxydibenzoylmethane | 0.5 |
| B: AMPHISOL | 3.0 |
| C: Distilled water | 74.8 |
| Propyleneglycol | 3.5 |
| Urea | 5.0 |
| Complex former (ethylenediaminetetraacetic acid, disodium salt) | 0.2 |
| D: Perfume 0.5% | q.s. |

| (d) Sun-screen milk (o/w) | |
|---|---|
| | Parts by weight |
| Preserving agent | q.s. |

The mixture A is heated to 85° C. on a steam-bath and then at this temperature B is added. The combined components of C are heated to 75° C. and then added to the mixture of A and B. The water losses are made up for after cooling to 25°–30° C. and then D is added. The mixture is further stirred until the temperature has fallen to 25°–30° C.

The following Example illustrates the preparation of the compound of formula I:

EXAMPLE 2

(a) 356 g (2 mol) of p-tert.butylbenzoic acid, 243 g (7.6 mol) of methyl alcohol and 35 g of sulphuric acid (96%) are added to a four-necked round flask which is provided with a stirrer and a condenser. The mixture is held for 8 hours at reflux temperature with slight stirring. The condenser is then replaced by a distillation column and the excess methyl alcohol is distilled off, towards the end under a slight vacuum but without the temperature exceeding 100° C. The mixture is cooled and poured on to ice. The phases are left to separate, the organic phase is washed with ice-water, with a saturated sodium carbonate solution in the presence of ice and finally with ice until neutral. The organic phase is dried over sodium sulphate and there is thus obtained a precipitate which weighs 393 g. By distillation on a Widmer column (120 mm) there are obtained 345 g (90% yield) of the ester of boiling point 76° C./0.02 mmHg.

(b) To a round flask which has been well dried and flushed with nitrogen are added 85 g (1.1 mol) of sodium amide (50% suspension in toluene) and 180 g of isopropyl ether and there are now added dropwise thereto at a temperature of 50°–60° C. 150.2 g (1 mol) of acetylanisole in 180 g of isopropyl ether. Reaction sets in immediately and a white paste-like mass forms. After completion of the addition, the mixture is stirred for a further 0.5 hour and then 192.3 g of p-tert.butylbenzoic acid methyl ester are added rapidly at 25°–30° C. The mixture is stirred for 0.5 hour at room temperature, then for 3 hours at 60°–70° C. and left to stand for 12 hours. 200 g of ice are then added and the mixture is acidified with 128 g (1.1 mol) of technical hydrochloric acid and 200 ml of ice-water. The mixture is stirred until the sodium salt of the product has dissolved. The phases are separated and the organic phase is washed with ice-water until neutral. The organic phase is concentrated on a rotary evaporator and there are thus recovered 290 g of isopropyl ether. The crude product weighs 347 g and still contains solvent. Recrystallisation from methanol yields 199.8 g (64.5%) of 4-(1,1-dimethylethyl)-4'-methoxydibenzoylmethane of melting point 83.5° C.

(c) 36 g (1.2 mol) of 80% sodium amide and 300 g of dry toluene are added to a round flask which was flushed with nitrogen. The mixture is heated to 50° C. and 150.2 g (1 mol) of acetylanisole in 309 g of toluene are added within 1.5 hours. After completion of the addition, the mixture is held at 50° C. for 15 minutes and there are then added thereto at this temperature within 1 hour 50 minutes 192.3 g (1 mol) of p-tert.butylbenzoic acid methyl ester. The mixture is stirred for a further 1 hour at 50° C. and then heated at 100° C. for 1 hour, after which time the product has separated out in the form of a solid precipitate. The mixture is left to stand for 12 hours and there are then added thereto 300 ml of ice-water followed by a mixture of 100 ml of pure hydrochloric acid and 250 ml of ice-water. The phases are separated and the organic phase is washed twice with water. The organic phase is dried over sodium sulphate and treated simultaneously with 20 g of active carbon. After filtration, the filtrate is concentrated until crystallisation begins. 50 ml of hexane are added, the mixture is cooled and then filtered over a Buchner funnel. After recrystallisation from 600 ml of methanol, there is obtained a total yield of 220.91 g (71.2%) of the desired 4-(1,1-dimethylethyl)-4'-methoxydibenzoylmethane of melting point 83.5° C.

I claim:

1. 4-(1,1-Dimethylethyl)-4'-methoxydibenzoylmethane.

2. A light-screen composition comprising an effective ultra violet absorbing amount of 4-(1,1-dimethylethyl)-4'-methoxydibenzoylmethane and at least one other organic material.

3. A light-screen composition according to claim 2 which contains 4-(1,1-dimethylethyl)-4'-methoxydibenzoylmethane in combination with UV B-filter.

4. A light-screen composition according to claim 2 or claim 3, wherein about 1 wt. % to 6 wt. % of 4-(1,1-dimethylethyl)-4'-methoxydibenzoylmethane is present.

5. A sun-screen composition comprising 2 wt. % to 5 wt. % of 4-(1,1-dimethylethyl)-4'-methoxydibenzoylmethane and 2.0 wt. % to 10.0 wt. % of 2-ethylhexyl p-methoxycinnamate.

6. A method for preparing a light screening composition which comprises incorporating 4-(1,1-dimethylethyl-4'-methoxydibenzoylmethane into a cosmetic base.

7. The method of claim 6 wherein the amount of 4-(1,1-dimethylethyl-4'-methoxydibenzoylmethane incorporated is between 1% and 6% by weight of the total composition.

8. The method of claim 6 wherein there is also incorporated a UV B-filter.

9. The method of claim 7 wherein there is also incorporated 1% to 12% by weight of 2-ethylhexyl-p-methoxycinnamate.

10. A topical preparation for application on the skin which comprises an effective amount of 4(1,1-dimethyl)-4'-methoxydibenzoylmethane as a UV-A absorber in a suitable carrier.

11. The preparation of claim 10 wherein the carrier is a suitable cosmetic base.

12. The preparation of claims 10 or 11 wherein the 4-(1,1-dimethylethyl)-4'-methoxydibenzoylmethane is present at a level of 1% by weight to 6% by weight.

13. The preparation of claims 10 or 11 wherein the 4-(1,1-dimethylethyl)-4'-methoxydibenzoylmethane is present at a level of 2% by weight to 5% by weight and wherein there is also present 2-ethylhexyl p-methoxycinnamate at a level of 2% by weight to 10% by weight.

14. A method for protecting the skin from the effects of U.V.-A radiation which comprises applying to the skin an effective amount of 4-(1,1-dimethylethyl)-4'-methoxydibenzoylmethane in a carrier suitable for application on the skin.

15. A method according to claim 14 wherein the carrier is a cosmetic base.

16. The method of claims 14 or 15 wherein the 4-(1,1-dimethylethyl)-4'-methoxydibenzoylmethane is applied as part of a formulation wherein it is present at a concentration of 1% by weight to 6% by weight of the formulation.

17. The method of claims 14 or 15 wherein the 4-(1,1-dimethylethyl)-4'-methoxydibenzoylmethane is applied as part of a formulation wherein it is present at a concentration of 2% by weight to 5% by weight and wherein there is also present 2-ethylhexyl p-methoxycinnamate at a level of 2% by weight to 10% by weight.

* * * * *